(12) United States Patent
Yan-Yong

(10) Patent No.: US 8,362,164 B2
(45) Date of Patent: Jan. 29, 2013

(54) MULTIFUNCTIONAL INITIATORS FOR ANIONIC POLYMERIZATION AND POLYMERS THEREFROM

(75) Inventor: Yan Yan-Yong, Copley, OH (US)

(73) Assignee: Bridgestone Corporation, Tokyo (JP)

(*) Notice: Subject to any disclaimer, the term of this patent is extended or adjusted under 35 U.S.C. 154(b) by 0 days.

(21) Appl. No.: 13/271,922

(22) Filed: Oct. 12, 2011

(65) Prior Publication Data

US 2012/0035336 A1 Feb. 9, 2012

Related U.S. Application Data

(63) Continuation of application No. 12/344,653, filed on Dec. 29, 2008, now abandoned.

(60) Provisional application No. 61/017,189, filed on Dec. 28, 2007.

(51) Int. Cl.
- C08F 4/08 (2006.01)
- C08F 4/48 (2006.01)
- C07D 211/92 (2006.01)
- C07D 255/02 (2006.01)
- C07D 401/06 (2006.01)

(52) U.S. Cl. ........ 526/217; 502/150; 502/200; 526/204; 526/236; 526/336; 526/340; 526/346; 526/347; 526/348; 528/396; 528/422; 528/423; 540/470; 540/474; 540/476; 546/184; 546/186; 546/246; 546/329; 564/452; 564/453; 564/454; 564/457; 564/461

(58) Field of Classification Search .......... 502/150, 502/200; 526/204, 217, 236, 336, 340, 346, 526/347, 348; 528/396, 422, 423; 540/470, 540/474, 476; 546/184, 186, 246, 329; 564/452, 564/453, 454, 457, 461

See application file for complete search history.

(56) References Cited

U.S. PATENT DOCUMENTS

| | | | |
|---|---|---|---|
| 4,935,471 A | 6/1990 | Halasa et al. |
| 5,149,457 A | 9/1992 | Smith |
| 5,153,159 A | 10/1992 | Antkowiak et al. |
| 5,153,271 A | 10/1992 | Lawson et al. |
| 5,210,144 A | 5/1993 | Lawson et al. |
| 5,210,145 A | 5/1993 | Lawson et al. |
| 5,239,009 A | 8/1993 | Halasa et al. |
| 5,254,628 A | 10/1993 | Lawson et al. |
| 5,268,413 A | 12/1993 | Antkowiak et al. |
| 5,310,798 A | 5/1994 | Lawson et al. |
| 5,329,005 A | 7/1994 | Lawson et al. |
| 5,332,810 A | 7/1994 | Lawson et al. |
| 5,334,665 A | 8/1994 | Lawson et al. |
| 5,354,822 A | 10/1994 | Antkowiak et al. |
| 5,393,721 A | 2/1995 | Kitamura et al. |
| 5,491,230 A | 2/1996 | Lawson et al. |
| 5,496,940 A | 3/1996 | Lawson et al. |
| 5,500,447 A | 3/1996 | Lawson et al. |
| 5,502,130 A | 3/1996 | Lawson et al. |
| 5,502,131 A | 3/1996 | Antkowiak et al. |
| 5,519,086 A | 5/1996 | Lawson et al. |
| 5,521,309 A | 5/1996 | Antkowiak et al. |
| 5,523,371 A | 6/1996 | Lawson et al. |
| 5,536,801 A | 7/1996 | Antkowiak et al. |
| 5,552,473 A | 9/1996 | Lawson et al. |
| 5,552,499 A | 9/1996 | Kitamura et al. |
| 5,574,109 A | 11/1996 | Lawson et al. |
| 5,578,542 A | 11/1996 | Lawson et al. |
| 5,610,228 A | 3/1997 | Lawson et al. |
| 5,610,237 A | 3/1997 | Lawson et al. |
| 5,616,704 A | 4/1997 | Lawson et al. |
| 5,643,848 A | 7/1997 | Lawson et al. |
| 5,674,798 A | 10/1997 | Kitamura et al. |
| 5,698,646 A | 12/1997 | Kitamura et al. |
| 5,723,533 A | 3/1998 | Lawson et al. |
| 5,726,308 A | 3/1998 | Hall et al. |

(Continued)

FOREIGN PATENT DOCUMENTS

| DE | 236321 | * 6/1986 |
|---|---|---|
| EP | 0590491 | 4/1994 |

(Continued)

OTHER PUBLICATIONS

Cheng, T. C., "Anionic Polymerization. VII. Polymerizatoin and Copolymerization with Lithium-Nitrogen-Bonded Initiator," In Anionic Polymerization; McGrath, J., Ed.; ACS Symposium Series, American Chemical Society: Washington, DC, Nov. 30, 1981; vol. 166, Chapter 33, pp. 513-528.*

(Continued)

Primary Examiner — Richard A Huhn
(74) Attorney, Agent, or Firm — Meredith E. Hooker; Jenny L. Sheaffer

(57) ABSTRACT

The embodiments of the invention relate to a multifunctional lithiated amine-containing compound comprising at least two molecules of lithiated amine in a molecule of the compound. In one embodiment, the compound has a formula

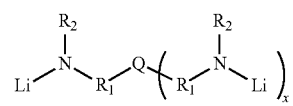

where x is an integer of 1 or more, Q is (a) an element selected from the group consisting of O, S, N, P and Si or (b) an alkylene group having from 1 to 20 methylene groups, and $R_1$ and $R_2$ are the same or different and are selected from the group consisting of alkyls, cycloalkyls and aralkyls containing from 1 to 20 carbon atoms. In another embodiment, the compound comprises cyclic lithio amines and has a formula:

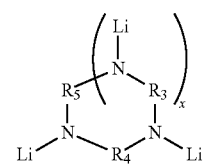

where x is 1 or more, $R_3$, $R_4$ and $R_5$ are the same or different and represent alkylene groups containing from 3 to 20 carbon atoms.

14 Claims, No Drawings

U.S. PATENT DOCUMENTS

| | | | |
|---|---|---|---|
| 5,736,617 | A | 4/1998 | Kerns et al. |
| 5,785,778 | A | 7/1998 | Lawson et al. |
| 5,786,441 | A | 7/1998 | Lawson et al. |
| 5,792,820 | A | 8/1998 | Lawson et al. |
| 5,883,183 | A | 3/1999 | Kitamura et al. |
| 5,912,343 | A | 6/1999 | Lawson et al. |
| 5,916,976 | A | 6/1999 | Kerns et al. |
| 5,923,044 | A | 7/1999 | Hall et al. |
| 5,932,662 | A | 8/1999 | Lawson et al. |
| 5,935,893 | A | 8/1999 | Lawson et al. |
| 5,955,531 | A | 9/1999 | Futamura |
| 5,959,048 | A | 9/1999 | Lawson et al. |
| 6,025,450 | A | 2/2000 | Lawson et al. |
| 6,046,288 | A | 4/2000 | Lawson et al. |
| 6,060,617 | A | 5/2000 | Hall et al. |
| 6,080,835 | A | 6/2000 | Lawson et al. |
| 6,084,025 | A | 7/2000 | Kitamura et al. |
| 6,349,753 | B1 | 2/2002 | Lawson et al. |
| 6,482,944 | B2 | 11/2002 | Schwindeman et al. |
| 6,515,087 | B2 | 2/2003 | Hsu et al. |
| 6,627,721 | B1 | 9/2003 | Rodewald et al. |
| 6,627,722 | B2 | 9/2003 | Rodewald et al. |
| 6,630,552 | B1 | 10/2003 | Rodewald et al. |
| 6,664,328 | B1 | 12/2003 | Rodewald et al. |
| 6,670,471 | B1 | 12/2003 | Rodewald et al. |
| 6,693,160 | B1 | 2/2004 | Halasa et al. |
| 6,753,447 | B2 | 6/2004 | Halasa et al. |
| 6,790,921 | B1 | 9/2004 | Rodewald et al. |
| 6,803,462 | B2 | 10/2004 | Rodewald et al. |
| 6,812,307 | B2 | 11/2004 | Halasa et al. |
| 6,825,306 | B2 | 11/2004 | Halasa et al. |
| 6,901,982 | B2 | 6/2005 | Halasa et al. |
| 6,927,269 | B2 | 8/2005 | Rodewald et al. |
| 6,933,358 | B2 | 8/2005 | Halasa et al. |
| 6,936,669 | B2 | 8/2005 | Halasa et al. |
| 6,995,224 | B2 | 2/2006 | Halasa et al. |
| 7,019,096 | B2 | 3/2006 | Dalphond et al. |
| 7,041,761 | B2 | 5/2006 | Halasa et al. |
| 7,108,033 | B2 | 9/2006 | Dalphond et al. |
| 7,125,934 | B1 | 10/2006 | Parker |
| 2002/0120082 | A1 | 8/2002 | Hsu et al. |

FOREIGN PATENT DOCUMENTS

| | | |
|---|---|---|
| EP | 0593049 | 4/1994 |
| GB | 2092163 | 8/1982 |
| GB | 2092163 A * | 8/1982 |

OTHER PUBLICATIONS

Bywater, S. et al., "Complexes of 1,2-Dipiperidinoethane with an Isoprenyllithium Oligomer", Macromolecules 1985, 18, 335-337.*

Banderman, F., et al., "Bifunctional Anionic Initiators: A Critical Study and Overview," Makromol. Chem., 186, pp. 2017-2024 (1985).

Cheng, T.C., "Anionic Polymerization, VII," ACS Symposium Series, vol. 166, Chapter 33, pp. 513-528, Nov. 30, 1981.

Gilman, Henry, et al. "Quantitative Analysis of of Alkyllithium Compounds," J Am Chem Soc., p. 1515 (1944).

Hirao, Akira, et al. "Precise Synthesis of Regular Asymmetric Star Polymers and Densely Branched Polymers With Starlike Structures by Means of Living Anionic Polymerization," Polymer Journal, vol. 34, No. 9, pp. 633-658 (2002).

Hofmans, J., et al., "Synthesis and Development of Dilithium Initiator and its Use for the Preparation of ABA-Block Copolymers in Non-Polar Medium: the Use of π-Complexing Additivtes," Polymer 46, 303-318 (2005).

Hsieh, H., et al., "Functionalized Polymers and Macromonomers," Anionic Polymerization: Principles and Practical Applications, pp: 267-306 (1996).

Huang, Der-Chi, et al., "Effects of Tetrahydorfuran as a Structure Modifier in Preparation of SBS Thermoplastic Block Copolymers in Cyclohexane," Journal of Applied Polymer Science, vol. 61, pp. 333-342 (Jul. 11, 1996).

Koulic, C., et al., Nanostructured Polyamide by Reactive Blending. 1. Effect of the Reactive Diblock Composition, Macromolecules 37, pp. 3459-3469 (2004).

Matmour, R., et al., "Tri- and Tetracarbanionic Initiators by a Lithium/halide Exchange Reaction: Application to Star-Polymer Synthesis," Living Polymerization, Agnew. Chem. Int. Ed., 44, 284-287 (2005).

Matmour, R., et al., "High Performance Poly(styrene-b-diene-b-styrene) Triblock Coploymers From a Hydrocarbon-Soluble and Additive-Free Dicarbanionic Initiator," J. Am. Chem. Soc., 128, 8158-8159 (2006).

Min, Cao et al., "Study of SSBR Prepared with Lithumamide Initiator," China Synthetic Rubber Industry, 25(2), p. 113 (2002).

Morita, K. et al., Anionic Polymerization of Dienes Using Lithiumamide Initiator Prepared by In-Situ Preparation, Fall National ACS Meeting, pp. 700-701 (1996).

Nagata, Nobuo, "Effect of Chemical Modification of Solution-Polymerized Rubber on Dynamic Mechanical Properties in Carbon-Black-Filled Vulcanizates," American Chemical Society, 60, 837-855 (1987).

Orr, Charles A., et al., "Flow-Induced Reactive Self-Assembly," Macromolecules, 30, (4), pp. 1243-1246 (1997).

Penn, L.S., et al., "Grafting Rates of Amine-Functionalized Polystyrenes Onto Epoxidized Silica Surfaces," Macromolecues, 33, 1105-1107 (2000).

Pispas, S., "Miktoarm Block Copolymer Formation via Ionic Interactions," Macromolecules, 36, pp. 759-763 (2003).

Pispas, S., "Anionic Polymerization of Isoprene, Butadiene and Styrene with 3-Dimethylaminopropyllithium," Polymer, vol. 36, Issue 15, pp. 3005-3011 (1995).

Quirk, R.P., et al., "Trifunctional Organolithium Initiator Based on 1, 3, 5-Tirs(1-Phenylethenyl)benzene. Synthesis of Functionalized, Three-Armed, Star-Branched Polystyrenes," Macromolecules, vol. 31, No. 23, 8016-8025 (1998).

Quirk, R.P., et al., "Recent Advances in Anionic Synthesis of Functionalized Elastomers Using Functionalized Alkylithium Initiators," Rubber Chem. Thechnol., 69(3), 444-461 (1996).

Quirk, et al., Anionic Synthesis of Chain-End Functionalized Polymers, Makromolekulare Chemie, Macromolecular Symposia, 32: pp. 47-59 (1990).

Sardelist, K., et al., "Graded Block and Randomized Polymers of Butadiene-Styrene," Polymer, vol. 25, 1011-1019 (1984).

Tsitsilianis, C., et al., "Synthesis of Coil-Rod-Coil Block Copolymers With the Aid of Anionic Polymerization," Macromolecular Rapid Communications, vol. 21, 1130-1135 (2000).

Vasilenko, N. G., et al., "Preparation of Multi-Arm Star Polymers with Polylithiated Carbosilane Dendrimers," Macromol. Chem. Phys. 199, 889-895 (1998).

Wang, Yurong et al., "Synthesis and Kinetic Behavior of Stereotriblock Polybutadiene Using Dilithium as Initiator," Journal of Applied Polymer Science, vol. 88, pp. 1049-1054 (2003).

Wang, Qiang, et al., "Formation of SBS Thermoplastic Block Copolymer Using Hexamethyleneimine Alkenyl Lithium (N-Li) Initiator," Journal of Applied Polymer Science, vol. 100, 81-88 (2006).

Young, Ronald N., et al., "Anionic Polymerizations of Non-Polar Monomers Involving Lithium," Advances in Polymer Science, 56, pp. 1-90 (1984).

Yu, J.M., et al., "Syndiotactic Poly(methyl methacrylate) (sPMMA)-Polybutadiene (PBD)-sPMMA Triblock Copolymers: Synthesis, Morphology, and Mechanical Properties," Macromolecules, vol. 29, 6090-6099 (1996).

Yu, J.S., et al., "Efficiency of the sec-Butyllithium/m-Diisopropenylbenzene Diadduct as an Anionic Polymerization Initiator of Apolar Solvents," Macromolecules 27, 5957-5963 (1994).

* cited by examiner

MULTIFUNCTIONAL INITIATORS FOR ANIONIC POLYMERIZATION AND POLYMERS THEREFROM

RELATED APPLICATION

This application is a Continuation of U.S. application Ser. No. 12/344,653, filed Dec. 29, 2008 now abandoned, and claims the benefit of the filing date of U.S. Provisional Patent Application Ser. No. 61/017,189, filed Dec. 28, 2007 both of which are incorporated herein by reference.

FIELD OF INVENTION

The embodiments of the invention relate to compounds that are useful as anionic polymerization initiators, and polymers therefrom.

BACKGROUND

Anionic polymerization techniques have been used to synthesize polymers that are useful in the manufacture of polymers, including rubbers. Certain initiators impart a functional group to the polymers, and these functional groups are believed to have a beneficial impact on the performance of polymers.

One type of anionic polymerization is anionic living polymerization. This form of polymerization is called "living" or "controlled polymerization" as the ability of a growing polymer chain to terminate has been removed. The result is that the polymer chains grow at a more constant rate than seen in traditional chain polymerization and their lengths remain very similar (i.e. they have a very low polydispersity index). Living polymerization is one method for synthesizing block copolymers since the polymer can be synthesized in stages, each stage containing a different monomer. Additional advantages are predetermined molar mass and control over end-groups.

Anionic polymerization using alkali metals, radical anions, alkyllithium compounds, and lithium amides as initiators for anionic polymerization of dienes and aromatic vinyls is known. Examples of such initiator systems are disclosed in the following references: H. L. Hsieh, R. P. Quirk, "Anionic Polymerization, principles and practical applications" Marcel Dekker, Inc., New York, 1996; R. P. Quirk, S. H. Jang, "*Recent advances in anionic synthesis of functionalized elastomers using functionalized alkylithium initiators*", Rubb. Chem. Thechnol., 1996, 69(3), 444-461; Y. S. Yu, R. Jérôme, R. Faft, Ph. Teyssié, "Efficiency of the sec-Butyllithium/m-Diisopropenylbenzene Diadduct as an Anionic Polymerization initiator in Apolar Solvents", Macromolecules, 1994, 27, 5957-5963; F. Bandermann, H. D. Speikamp, L. Weigel, "Bifunctional anionic initiators: A critical study and overview", Makromol. Chem. 1985, 186, 2017-2024; and Rachid Matmour, Arvind S. More, Prakash P. Wadgaonkar, and Yves Gnanou, "High performance poly (styrene-b-diene-b-styrene) triblock copolymers from a hydrocarbon-soluble and additive-free dicarbanionic initiator", J. Am. Chem. Soc. 2006, 128(25), 8158-8159. U.S. Pat. No. 5,329,005, issued Jul. 12, 1994, and entitled "Soluble Anionic Polymerization Initiators and Preparation Thereof," discloses mono lithio amine initiators.

Organo dilithio compounds are of special interest as bifunctional initiators in the anionic polymerization of dienes. The sec-butyllithium/1,3-diisopropenylbenzene/triethylamine adduct, for example, is saved as difunctional lithium initiator (DiLi). However, this DiLi system requires polar additive triethylamine ($Et_3N$) as solvent to prevent the aggregation of 1,3-diisopropenylbenzene, and combine with sec-butyl lithium, the major drawbacks of which are that it requires pre-reaction steps to synthesize the initiator, low initiator concentration, bi-modal initiation, and difficulty to make the low vinyl polybutadiene polymers.

Therefore, although alkali metal, mono-functional initiators such as alkyl lithium and lithium amides are known, and DiLi systems are known, multifunctional lithiated amine-containing initiators are not well known.

SUMMARY OF THE INVENTION

The embodiments of the invention relate to multifunctional lithiated amine-containing compound comprising at least two molecules of lithiated amine in a molecule of the compound, wherein the compound does not contain any active hydrogen that can react with carbon-lithium or nitrogen-lithium species. In some embodiments, the compound has a formula:

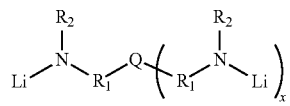

where x is an integer of 1 or more, Q is (a) an element selected from the group consisting of O, S, N, P and Si or (b) an alkylene group having from 1 to 20 methylene groups, and $R_1$ and $R_2$ are the same or different and are selected from the group consisting of alkyls, cycloalkyls and aralkyls containing from 1 to 20 carbon atoms. In one variation, nitrogen in the compound shown above forms part of a ring.

The compound could have the formula:

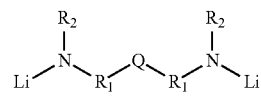

wherein Q divalent.
The compound could have the formula:

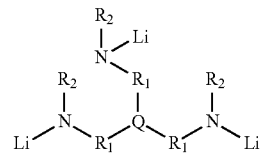

wherein Q is trivalent.
The compound could have the formula:

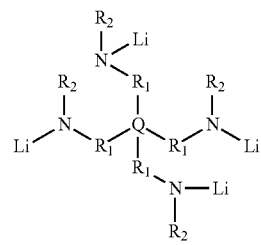

wherein Q is tetravalent.

The compound could have the formula wherein Q is a dendrimer or a nano-material, wherein the dendrimer or the nano-material has a plurality of sites for forming chemical bonds.

The compound could have the formula wherein at least of one of the at least two molecules of lithiated amine comprises a functionalized piperidine, a functionalized piperazine, or a functionalized pyrrolidine.

The compound could have the formula wherein the formula represents Li-4,4'-trimethylenedipiperidine-Li.

In other embodiments, the compound comprises cyclic lithio amines and has a formula:

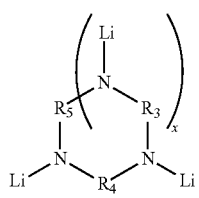

where x is 1 or more, $R_3$, $R_4$ and $R_5$ are the same or different and represent alkylene groups containing from 3 to 20 carbon atoms.

Yet other embodiments of the invention relate to a polymer comprising multifunctional lithiated amine-containing compound comprising at least two molecules of lithiated amine in a molecule of the compound, wherein the compound does not contain any active hydrogen that can react with carbon-lithium or nitrogen-lithium species. The polymer could comprise butadiene or styrene and a polymerization terminator. The polymer could comprise both styrene and butadiene. Preferably, the polymer has tan δ measured by a rotorless shear rheometer of less than 0.1 for shear rate sweeps performed at a strain set between 2 to 14% strain.

The polymer could have the compound having a formula

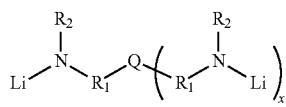

where x is an integer of 1 or more, Q is (a) an element selected from the group consisting of O, S, N, P and Si or (b) an alkylene group having from 1 to 20 methylene groups, and $R_1$ and $R_2$ are the same or different and are selected from the group consisting of alkyls, cycloalkyls and aralkyls containing from 1 to 20 carbon atoms.

The polymer could have the compound comprising cyclic lithio amines and having a formula:

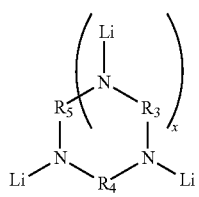

where x is 1 or more, $R_3$, $R_4$ and $R_5$ are the same or different and represent alkylene groups containing from 3 to 20 carbon atoms.

Another embodiment relates to a method of manufacturing a multifunctional lithiated amine-containing compound comprising at least two molecules of lithiated amine in a molecule of the compound, the method comprising reacting lithium or a lithium-containing compound with an amine-containing compound having at least two nitrogen atoms, wherein the compound does not contain any active hydrogen that can react with carbon-lithium or nitrogen-lithium species. Preferably, the method uses an amine-containing compound is 4,4'-trimethylenedipiperidine.

Another embodiment relates to a method of preparing a polymer by employing anionic polymerization comprising: (i) providing monomer including conjugated dienes; (ii) providing a polymerization medium including a non-polar solvent; (iii) providing an initiator comprising a multifunctional lithiated amine-containing compound comprising at least two molecules of lithiated amine in a molecule of the compound, wherein the compound does not contain any active hydrogen that can react with carbon-lithium or nitrogen-lithium species; and (iv) contacting the monomer and initiator within the polymerization medium. Preferably in the method, the initiator is generated in-situ during the preparation of the polymer. Preferably in the method, the anionic polymerization is a mono-modal living polymerization. Preferably in the method, the contacting the monomer and initiator within the polymerization medium results in a living polymer, and further comprising the step of contacting the living polymer with a polymerization terminator.

Preferably in the method of preparing a polymer, the compound has a formula:

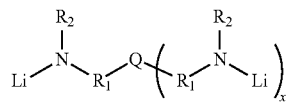

where x is an integer of 1 or more, Q is (a) an element selected from the group consisting of O, S, N, P and Si or (b) an alkylene group having from 1 to 20 methylene groups, and $R_1$ and $R_2$ are the same or different and are selected from the group consisting of alkyls, cycloalkyls and aralkyls containing from 1 to 20 carbon atoms.

Preferably in the method of preparing a polymer, the compound has a formula:

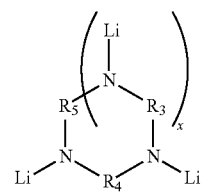

where x is 1 or more, $R_3$, $R_4$ and $R_5$ are the same or different and represent alkylene groups containing from 3 to 20 carbon atoms.

Yet another embodiment of the invention relates to tire component comprising a vulcanizate residue of the polymer of the embodiments of the invention.

Additional advantages of this invention will become readily apparent to those skilled in this art from the following detailed description, wherein only the preferred embodiments of this invention is shown and described, simply by way of illustration of the best mode contemplated for carrying out this invention. As will be realized, this invention is capable of other and different embodiments, and its details are capable of modifications in various obvious respects, all without departing from this invention. Accordingly, the drawings and description are to be regarded as illustrative in nature and not as restrictive.

DETAILED DESCRIPTION

As used in the specification and claims, the singular forms "a", "an" and "the" include plural references unless the context clearly dictates otherwise. For example, the term "a molecule" may include a plurality of molecules unless the context clearly dictates otherwise.

The term "molecule" generally refers to group of at least two atoms in a definite arrangement held together by a chemical bond. A molecule includes a macromolecule or polymer as described herein.

The term "amine" refers to a chemical compound containing nitrogen.

"Monomer" as used herein refers to a repeating structural unit that is used to a form a polymer. The formation of a polymer from monomer units takes place by "monomer addition cycle," which is a cycle comprising the chemical reactions necessary to produce covalent attachment of a monomer to another monomer, a nascent polymer or linker molecule, such as to elongate the polymer with the desired chemical bond. A "linker" molecule refers to any of those molecules described supra and preferably should be about 4 to about 40 atoms long to provide sufficient exposure. The linker molecules may be, for example, aryl acetylene, ethylene glycol oligomers containing 2-10 monomer units, diamines, diacids, amino acids, among others, and combinations thereof. Alternatively, the linkers may be the same molecule type as that being synthesized (i.e., nascent polymers).

Monomers may have different groups such as "alkyl," etc. The term "alkyl" refers to those groups such as methyl, ethyl, propyl, butyl etc, which may be linear, branched or cyclic. The term "alkoxy" refers to groups such as methoxy, ethoxy, propoxy, butoxy, etc., which may be linear, branched or cyclic. The term "lower" as used in the context of lower alkyl or lower alkoxy refers to groups having one to six carbons. The term "aryl" refers to an aromatic hydrocarbon ring to which is attached an alkyl group. The term "aryloxy" refers to an aromatic hydrocarbon ring to which is attached an alkoxy group. One of ordinary skill in the art would readily understand these terms.

Monomer that can be polymerized by the initiator compounds of the present invention include any monomer capable of being polymerized according to anionic polymerization techniques. These monomers include those that lead to the formation of elastomeric homopolymers or copolymers. Suitable monomers include, without limitation, conjugated $C_4$-$C_{12}$ dienes (optionally together with $C_8$-$C_{18}$ monovinyl aromatic monomers) and $C_6$-$C_{20}$ trienes. Examples of conjugated diene monomers include, without limitation, 1,3-butadiene, isoprene, 1,3-pentadiene, 2,3-dimethyl-1,3-butadiene, and 1,3-hexadiene. A non-limiting example of trienes includes myrcene. Aromatic vinyl monomers include, without limitation, styrene, α-methyl styrene, p-methylstyrene, and vinylnaphthalene. When preparing elastomeric copolymers, such as those containing conjugated diene monomers and aromatic vinyl monomers, the conjugated diene monomers and aromatic vinyl monomers are normally used at a ratio of 95:5 to 50:50, and preferably 95:5 to 65:35.

The lower molecular weight compounds built from monomers are also referred to as dimers, trimers, tetramers, quadramers, pentamers, octamers, 20-mers, etc. if they have 2, 3, 4, 5, 8, or 20 monomer units, respectively. Any number of these monomer units may be indicated by the appropriate prefix, e.g., decamer, being a 10-unit monomer chain or polymer. Larger numbers are often stated in English in lieu of Greek.

The term "polymer" refers to a molecule formed by combining a plurality of monomers. Generally, a polymer is a substance composed of molecules with large molecular mass composed of repeating structural units, or monomers, connected by covalent chemical bonds. The structural properties of a polymer relate to the physical arrangement of monomers along the backbone of the chain. Structure has a strong influence on the other properties of a polymer. For example, a linear chain polymer may be soluble or insoluble in water depending on whether it is composed of polar monomers (such as ethylene oxide) or nonpolar monomers (such as styrene). On the other hand, two samples of natural rubber may exhibit different durability even though their molecules comprise the same monomers.

The polymers of the embodiments of this invention include polymers that contain only a single type of monomer are known as homopolymers, while polymers containing a mixture of monomers are known as copolymers. The copolymers could be alternating copolymers possessing regularly alternating monomer units; periodic copolymers have monomer unit types arranged in a repeating sequence; random copolymers have a random sequence of monomer unit types; statistical copolymers have monomer units arranged according to a known statistical rule; and block copolymers have two or more homopolymer subunits linked by covalent bonds. Block copolymers with two or three distinct blocks are called diblock copolymers and triblock copolymers, respectively.

The polymers of the embodiments of this invention include straight chain or linear polymer, composed of a single main chain and a branched polymer molecule composed of a main chain with one or more substituent side chains or branches. Special types of branched polymers include star polymers, comb polymers, and brush polymers. A "brush polymer" ordinarily refers to polymer films comprising chains of polymers that are attached to the surface of a substrate. The polymeric brush could be functionalized polymer films which comprise functional groups such as hydroxyl, amino, carboxyl, thiol, amide, cyanate, thiocyanate, isocyanate and isothio cyanate groups, or a combination thereof, on the polymer chains at one or more predefined regions. The polymeric brushes of the embodiment of the invention are capable of attachment or stepwise synthesis of macromolecules thereon. The polymer could also contain a side chain that has a different composition or configuration than the main chain, in which case the polymer is called a graft or grafted polymer.

A "free radical initiator" or "initiator" is a compound that can provide a free radical under certain conditions such as heat, light, or other electromagnetic radiation, which free radical can be transferred from one monomer to another and thus propagate a chain of reactions through which a polymer may be formed. Several free radical initiators are known in the art, such as azo, nitroxide, and peroxide types, or those comprising multi-component systems.

"Living polymerization" is defined as a polymerization process wherein chain initiation and chain propagation occur without significant chain termination reactions. Each initiator molecule produces a growing monomer chain which continuously propagates until all the available monomer has been reacted. One type of living polymerization is living free radical polymerization, which differs from conventional free radical polymerization where chain initiation, chain propagation and chain termination reactions occur simultaneously and polymerization continues until the initiator is consumed. Living free radical polymerization facilitates control of molecular weight and molecular weight distribution. Living free radical polymerization techniques, for example, involve reversible end capping of growing chains during polymerization. One example is atom transfer radical polymerization (ATRP).

A "polymerization terminator" is a compound that prevents a polymer chain from further polymerization. These compounds may also be known as "terminators," or "capping agents" or "inhibitors." Various polymerization terminators are known in the art.

The term "chemical bond" means attached through a bond that is covalent or ionic.

A "dendrimer" is repeatedly branched molecules (dendritic molecules). Dendritic molecules are repeatedly branched species that are characterized by their structure perfection. The latter is based on the evaluation of both symmetry and polydispersity. The area of dendritic molecules can roughly be divided into the low-molecular weight and the high-molecular weight species. The first category includes dendrimers and dendrons whereas the second encompasses dendronized polymers, hyperbranched polymers, and brush-polymers (also called bottle-brushes). The name "dendrimer" comes from the dendron, meaning "tree". Synonymous terms are arborols and cascade-molecules. Dendrimers and dendrons are generally repeatedly branched, monodisperse, and usually highly symmetric compounds. There is no apparent difference in defining dendrimer and dendron. A dendron usually contains a single chemically addressable group that is called focal point.

A "nano-material" as used herein refers to a structure, a device or a system having a dimension at the atomic, molecular or macromolecular levels, in the length scale of approximately 1-100 nanometer range. Preferably, a nano-material has properties and functions because of the size and can be manipulated and controlled on the atomic level.

The term "hysteresis" means the difference between the energy applied to deform an article made from a material and the energy released as the article returns to its initial, non-deformed state. Preferably, the hysteresis data in the embodiments of this invention relate to an elastomeric (rubbery) material.

One or more embodiments of the invention relate to a multi-functional initiator for living polymerization of a monomer. The multi-functional initiator includes bi- and tri-functional initiators for anionic living polymerization of dienes and/or aromatic vinyl monomers. Because of the "living" nature of this new initiation system, it can be used for synthesis of X-SBR-X, X-PB-X (where X, SBR and PB represent a polymerization terminator, styrene butadiene rubber, and polybutadiene, respectively) functional and star-shaped functional polymers having low rolling resistance, synthesis of AB-diblock or ABA-triblock copolymers (where A and B represent block segments), and rational design micelle-nanoparticles, which can be widely used for tire and non-tire applications. The A and B blocks could be styrene, butadiene, isoprene such that the block copolymers could be SBS, SIS, SB, etc.

Other embodiments of this invention relate to polymers and tires having low rolling resistance, which is reflected by low tan delta of the polymer measured by a rheometer such as a rotorless shear rheometer (RPA). One of the functions of the RPA is to be used as a processability tester. The RPA molds the uncured rubber formulation in a sealed pressurized cavity and has a special direct drive motor that oscillates the lower die sinusoidally over a range of preprogrammed strains, frequencies and temperatures. RPA shear rate sweeps (through variations in frequency) are commonly performed at a fixed strain set between 2 to 14% strain to measure the drop in complex and real dynamic viscosity with increasing shear rate for rubber compounds. Also, sometimes very high strain sweeps are performed with the RPA. Other outputs from the RPA include: G' for storage (elastic) modulus, G" for loss (viscous) modulus, S' for elastic torque, and S" for viscous torque. An additional output, tan delta, is derived from either dividing G" by G' or dividing S" by S'. The parameter tan delta is dimensionless, without units.

In the embodiments of the invention, the initiator comprises a multifunctional lithiated amine having at least two lithiated amines in one molecule of the initiator.

In general, the embodiments of the invention relate to a hydrocarbon solvent soluble, anionic polymerization multi-lithio amine initiators which comprise at least two or more lithio amine in one molecular and having the general formula:

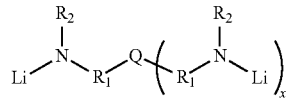

where x is an integer of 1 or more, Q is (a) an element selected from the group consisting of O, S, N, P and Si or (b) an alkylene group having from 1 to 20 methylene groups, and $R_1$ and $R_2$ are the same or different and are selected from the group consisting of alkyls, cycloalkyls and aralkyls containing from 1 to 20 carbon atoms.

In other embodiments, the compound has the following formulas:

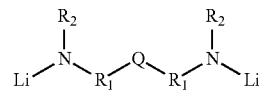

where Q is divalent (e.g., methylene groups, O or S)

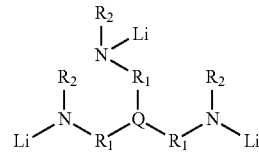

where Q is trivalent (e.g., N, or P), and

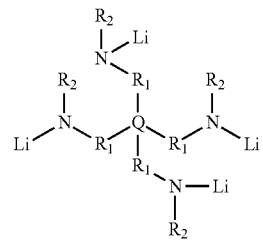

where Q is tetravalent (e.g., C or Si).

In other embodiments, the anionic polymerization multi-lithio amine initiators which comprise at least two or more lithio amine in one molecule have cyclic lithio amines and have the following general formula:

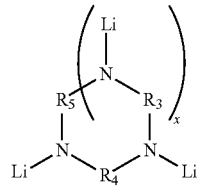

where x is 1 or more, $R_3$, $R_4$ and $R_5$ are the same or different and represent alkylene groups containing from 3 to 20 carbon atoms.

In one embodiment of the invention, 4,4'-trimethylenedipiperidine commercially available reagent from Aldrich was successfully metalated with n-BuLi (n-butyl lithium) and used for initiating the living polymerization of dienes and/or aromatic vinyls in hexane solution without any polar additives as shown in Scheme 1.

The advantages of this new difunctional initiator are: a) mono-modal living system such that the polymer formed has a mono-modal molecular weight as characterized by gel permeation chromatography (GPC); b) in-situ generation of the initiator; and c) absence of polar additives. These advantages are especially useful for making head and tail di-functional polymers and SBS-triblock copolymers with low $T_g$ polybutadiene unit in the middle of the triblock.

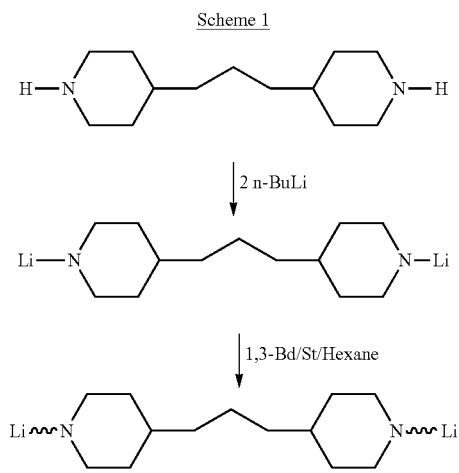

In another embodiment, a series of polyamines similar to 4,4'-trimethylenedipiperidine (TMDP) can be used as di- or tri-N—Li initiators for anionic polymerization of 1,3-butadiene and styrene. Examples of the di- and tri-lithio amine initiators include (scheme 2), but are not limited to, dilithio N,N'-diethyl-1,3-propanediamine (Li-DEPDA-Li), dilithio N,N'-diisopropyl-1,3-propanediamine (Li-DPPDA-Li), dilithio N,N'-diethyl-2-butene-1,4-diamine (Li-DEBDA-Li), trilithio tris[2-(methylamino)ethyl]amine (Tri-Li-TMAEA), trilithio tris[2-(isopropylamino)ethyl]amine (Tri-Li-TPAEA), and trilithio-1,5,9-triazacyclododecane (Tri-Li-TACD).

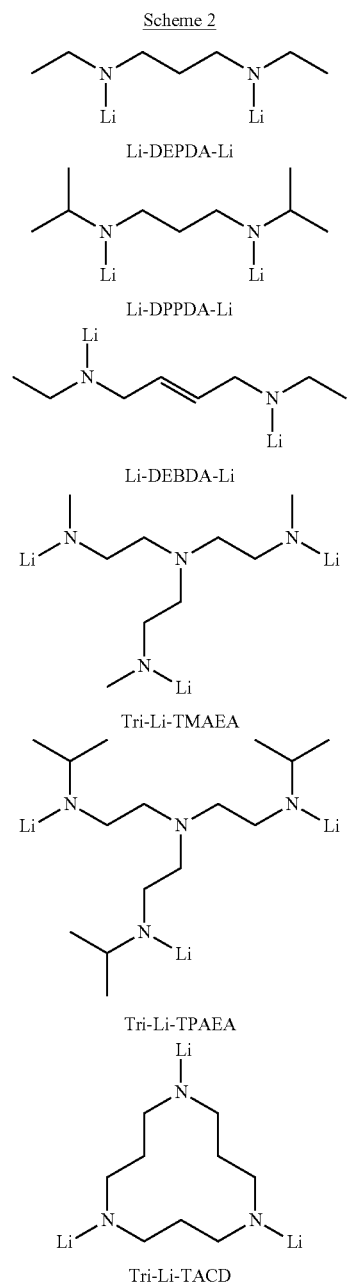

In one or more embodiments, the initiator solutions of this invention include one or more of the initiator compounds defined above and a solvent that includes an aliphatic or cycloaliphatic solvent. These initiator solutions may be useful for preparing, storing, using, transporting, or delivering the initiator compounds of this invention. Some representative examples of suitable aliphatic solvents include n-pentane, n-hexane, n-heptane, n-octane, n-nonane, n-decane, isopentane, isohexanes, isoheptanes, isooctanes, 2,2-dimethylbutane, petroleum ether, kerosene, petroleum spirits, and mixtures thereof. Some representative examples of suitable cycloaliphatic solvents include cyclopentane, cyclohexane, methylcyclopentane, methylcyclohexane, and mixtures thereof. Mixtures of aliphatic and cycloaliphatic solvents may be employed.

In one or more embodiments, the solvent employed in the initiator solutions may also include an ether solvent. Useful ethers include tetrahydrofuran (THF), 1,2-dimethoxyethene, 1,6-dimethoxyhexane, 1,3-dioxane, 1,4-dioxane, anisole, ethoxybenzene, and mixtures thereof.

The mixtures of aliphatic or cycloaliphatic solvents and ether solvents may include up to about 65 volume percent aliphatic or cycloaliphatic solvent, in other embodiments up to about 55 volume percent aliphatic or cycloaliphatic solvents, or in other embodiments up to about 45 volume percent aliphatic or cycloaliphatic solvent, with the remainder including an ether; in these or other embodiments, the mixtures of aliphatic or cycloaliphatic solvents and ether solvents include at least 10 volume percent, in other embodiments at least 20 volume percent, in other embodiments at least 30 volume percent, and in other embodiments at least 40 volume percent aliphatic or cycloaliphatic solvent.

In one or more embodiments, the initiator solutions of this invention may include 0.6 molar initiator solutions including up to about 30 volume percent aliphatic or cycloaliphatic solvent, where the initiator compound is soluble and stable at room temperature and standard pressure for 24 hours. In other embodiments, initiator solutions may include 0.3 molar initiator solutions including up to about 65 volume percent, and in other embodiments up to about 70 volume percent aliphatic or cycloaliphatic solvent, where the initiator compound is soluble and stable at room temperature and standard pressure for 24 hours.

In one or more embodiments, the lithiated amine species may be prepared in situ (i.e., in the presence of the monomer to be polymerized) or in advance of contacting the initiator with the monomer to be polymerized. When prepared in advance, the lithiated amine species may be directly employed in the polymerization reaction by delivering the lithiated amine species to the monomer immediately or within a short period of time (e.g., less than 5 minutes). In other embodiments, the lithiated amine species may be stored prior to use in the polymerization reaction period. In one or more embodiments, the initiator solution can be stored at a temperature from about −25 to about 25° C., or in other embodiments from about −10 to about +10° C. for at least one week, or in other embodiments at least two weeks. In yet other embodiments, the lithiation reaction can take place in the presence of a small amount of monomer (e.g., 1 to about 100 mole per mole of lithium), and then this solution can be subsequently contacted with the remainder of the monomer to be polymerized.

The initiator compounds of this invention can be used to polymerize monomer including conjugated dienes according to conventional anionic polymerization techniques. In general, these processes include combining, introducing, or contacting the initiator compound with monomer. This may take place in the presence of a solvent. The process results in a living polymer that can be protonated or further functionalized.

The amount of initiator employed in conducting anionic polymerizations can vary widely based upon the desired polymer characteristics. In one or more embodiments, from about 0.1 to about 100, in other embodiments from about 0.33 to about 10, and in other embodiments from about 0.2 to 1.0 mmol of lithium per 100 g of monomer is employed.

The polymerization processes of this invention may be conducted in non-polar solvents and mixtures of non-polar solvents with polar-solvents including those discussed above. In order to promote randomization in copolymerization and to control vinyl content, a polar coordinator may be added to the polymerization ingredients. Amounts may range between 0 and 90 or more equivalents per equivalent of lithium. The amount may depend on the amount of vinyl desired, the level of styrene employed and the temperature of the polymerization, as well as the nature of the specific polar coordinator (modifier) employed. Suitable polymerization modifiers include ethers or amines to provide the desired microstructure and randomization of the comonomer units.

Compounds useful as polar coordinators include those having an oxygen or nitrogen heteroatom and a non-bonded pair of electrons. Examples include dialkyl ethers of mono and oligo alkylene glycols; "crown" ethers; tertiary amines such as tetramethylethylene diamine (TMEDA); linear THF oligomers; and the like. Specific examples of compounds useful as polar coordinators include tetrahydrofuran (THF), linear and cyclic oligomeric oxolanyl alkanes such as 2,2-bis (2'-tetrahydrofuryl)propane, di-piperidyl ethane, dipiperidyl methane, hexamethylphosphoramide, N—N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, incorporated herein by reference.

By reacting anionic initiators according to this reaction with certain unsaturated monomers, a living polymer is propagated into a polymeric structure. Throughout formation and propagation of the polymer, the polymeric structure may be anionic and "living." A new batch of monomer subsequently added to the reaction can add to the living ends of the existing chains and increase the degree of polymerization. A living polymer, therefore, includes a polymeric segment having a living or reactive end. Anionic polymerization is further described in George Odian, Principles of Polymerization, ch. 5 (3rd Ed. 1991), or Panek 94 J. Am. Chem. Soc., 8768 (1972), which are incorporated herein by reference.

Anionically polymerized living polymers can be prepared by either batch or continuous methods. A batch polymerization is begun by charging a blend of monomer(s) and normal alkane solvent to a suitable reaction vessel, followed by the addition of the polar coordinator (if employed) and an initiator compound. The reactants may be heated to a temperature of from about 20 to about 130° C. and the polymerization may be allowed to proceed for from about 0.1 to about 24 hours. This reaction produces a reactive polymer having a reactive or living end. In one or more embodiments, at least about 30% of the polymer molecules contain a living end, in other embodiments at least about 50% of the polymer molecules contain a living end, and in other embodiments at least about 80% contain a living end.

The living polymer can be protonated or subsequently functionalized or coupled. Protonation can occur by the addition of any compound that can donate a proton to the living end. Examples include water, isopropyl alcohol, and methyl alcohol.

In other embodiments, the living polymer can be terminated with a compound that will impart a functional group to the terminus of the polymer. Useful functionalizing agents include those conventionally employed in the art. Types of compounds that have been used to end-functionalize living polymers include carbon dioxide, benzophenones, benzaldehydes, imidazolidones, pyrrolidinones, carbodiimides, ureas, isocyanates, and Schiff bases including those disclosed in U.S. Pat. Nos. 3,109,871, 3,135,716, 5,332,810, 5,109,907, 5,210,145, 5,227,431, 5,329,005, 5,935,893, which are incorporated herein by reference. Specific examples include trialkyltin halides such as triisobutyltin chloride, as disclosed in U.S. Pat. Nos. 4,519,431, 4,540,744, 4,603,722, 5,248,722, 5,349,024, 5,502,129, and 5,877,336, which are incorporated herein by reference. Other examples include cyclic amino compounds such as hexamethyleneimine alkyl chloride, as disclosed in U.S. Pat. Nos. 5,786,441, 5,916,976 and 5,552,473, which are incorporated herein by reference. Other examples include N-substituted aminoketones, N-substituted thioaminoketones, N-substituted aminoaldehydes, and N-substituted thioaminoaldehydes, including N-methyl-2-perrolidone or dimethylimidazolidinone (i.e., 1,3-dimethylethyleneurea) as disclosed in U.S. Pat. Nos. 4,677,165, 5,219,942, 5,902,856, 4,616,069, 4,929,679, 5,115,035, and 6,359,167, which are incorporated herein by reference. Additional examples include sulfur-containing or oxygen containing azaheterocycles such as disclosed in WO 2004/020475, U.S. Ser. No. 60/644,164 and U.S. Pat. No. 6,596,798, which are incorporated herein by reference. Other examples include boron-containing terminators such as disclosed in U.S. Ser. No. 60/591,065, which is incorporated herein by reference. Still other examples include cyclic siloxanes such as hexamethylcyclotrisiloxane, including those disclosed in copending U.S. Ser. No. 60/622,188, which is incorporated herein by reference. Further, other examples include α-halo-θ-amino alkanes, such as 1-(3-bromopropyl)-2,2,5,5-tetramethyl-1-aza-2,5-disilacyclopentane, including those disclosed in copending U.S. Ser. Nos. 60/624,347 and 60/643,653, which are incorporated herein by reference.

Useful coupling agents that can be employed in combination with the functionalizing agent include any of those coupling agents known in the art including, but not limited to, tin tetrachloride, tetraethyl ortho silicate, tetraethoxy tin, silicon tetrachloride, and mixtures thereof. In certain embodiments, the functionalizing agent can be employed in combination with other coupling or terminating agents. The combination of functionalizing agent with other terminating agent or coupling agent can be in any molar ratio.

In one embodiment, the functionalizing agent may be added to the living polymer cement (i.e., polymer and solvent) once a peak polymerization temperature, which is indicative of nearly complete monomer conversion, is observed. Because live ends may self-terminate, the functionalizing agent may be added within about 25 to 35 minutes of the peak polymerization temperature.

The amount of functionalizing agent employed to prepare the functionalized polymers is best described with respect to the equivalents of lithium or metal cation associated with the initiator. For example, the moles of functionalizing agent per mole of lithium may be about 0.3 to about 2, in other embodiments from about 0.6 to about 1.5, in other embodiments from about 0.7 to about 1.3, in other embodiments from about 0.8 to about 1.1, and in other embodiments from about 0.9 to about 1.0.

After formation of the polymer, a processing aid and other optional additives such as oil can be added to the polymer cement. The polymer and other optional ingredients may then be isolated from the solvent and optionally dried. Conventional procedures for desolventization and drying may be employed. In one embodiment, the polymer may be isolated from the solvent by steam desolventization or hot water coagulation of the solvent followed by filtration. Residual solvent may be removed by using conventional drying techniques such as oven drying or drum drying. Alternatively, the cement may be directly drum dried.

In one or more embodiments, the use of the initiator compounds of the present invention to anionically polymerize monomer can lead to the formation of functionalized polymers. In other words, polymers bearing a residue of the initiator compounds of the present invention can be formed, where the residue is located at the head of the polymer (i.e., at the location where the polymer chain was first propagated). In one or embodiments, these polymers may include high molecular weight polymers. In one or more embodiments, the weight average molecular weight (Mw) of the polymers may be in excess of 50 kg/mole, in other embodiments in excess of 100 kg/mole, in other embodiments in excess of 150 kg/mole, in other embodiments in excess of 200 kg/mole, and in other embodiments from about 50 to about 400 kg/mole. In these or other embodiments, the polymers may have a number average molecular weight (Mn) in excess of 40 kg/mole, in other embodiments in excess of 80 kg/mole, in other embodiments in excess of 120 kg/mole, in other embodiments in excess of 180 kg/mole, and in other embodiments in from about 40 to about 300 kg/mole in. In these or other embodiments, the polymers may have a molecular weight distribution, i.e., polydispersity index (Mw/Mn), of less than 2.0, in other embodiments less than 1.5, in other embodiments less than 1.3, in other embodiments less than 1.2, in other embodiments less than 1.1, and in other embodiments less than 1.0.

The functionalized polymers of this invention are particularly useful in preparing tire components. These tire components can be prepared by using the functionalized polymers of this invention alone or together with other rubbery polymers. Other rubbery elastomers that may be used include natural and synthetic elastomers. The synthetic elastomers typically derive from the polymerization of conjugated diene monomers. These conjugated diene monomers may be copolymerized with other monomers such as vinyl aromatic monomers. Other rubbery elastomers may derive from the polymerization of ethylene together with one or more .alpha.-olefins and optionally one or more diene monomers.

Useful rubbery elastomers include natural rubber, synthetic polyisoprene, polybutadiene, polyisobutylene-co-isoprene, neoprene, poly(ethylene-co-propylene), poly(styrene-co-butadiene), poly(styrene-co-isoprene), and poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof. These elastomers can have a myriad of macromolecular structures including linear, branched and star shaped. Other ingredients that are typically employed in rubber compounding may also be added.

The rubber compositions may include fillers such as inorganic and organic fillers. The organic fillers include carbon black and starch. The inorganic fillers may include silica, aluminum hydroxide, magnesium hydroxide, clays (hydrated aluminum silicates), and mixtures thereof.

A multitude of rubber curing agents may be employed, including sulfur or peroxide-based curing systems. Curing agents are described in 20 Kirk-Othmer, Encyclopedia of Chemical Technology, 365-468, (3rd Ed. 1982), particularly Vulcanization Agents and Auxiliary Materials, 390-402, and A. Y. Coran, Vulcanization in Encyclopedia of Polymer Science and Engineering, (2nd Ed. 1989), which are incorporated herein by reference. Vulcanizing agents may be used alone or in combination.

Other ingredients that may be employed include accelerators, oils, waxes, scorch inhibiting agents, processing aids, zinc oxide, tackifying resins, reinforcing resins, fatty acids such as stearic acid, peptizers, and one or more additional rubbers.

These stocks are useful for forming tire components such as treads, subtreads, sidewalls, body ply skins, bead filler, and the like. Preferably, the functional polymers are employed in tread formulations. In one or more embodiments, these tread formulations may include from about 10 to about 100% by weight, in other embodiments from about 35 to about 90% by weight, and in other embodiments from about 50 to 80% by weight of the functional polymer based on the total weight of the rubber within the formulation. In one or more embodiments, the preparation of vulcanizable compositions and the construction and curing of the tire is not affected by the practice of this invention.

In one or more embodiments, the vulcanizable rubber composition may be prepared by forming an initial masterbatch that includes the rubber component and filler (the rubber component optionally including the functionalized polymer of this invention). This initial masterbatch may be mixed at a starting temperature of from about 25° C. to about 125° C. with a discharge temperature of about 135° C. to about 180° C. To prevent premature vulcanization (also known as scorch), this initial masterbatch may exclude vulcanizing agents. Once the initial masterbatch is processed, the vulcanizing agents may be introduced and blended into the initial masterbatch at low temperatures in a final mix stage, which preferably does not initiate the vulcanization process. Optionally, additional mixing stages, sometimes called remills, can be employed between the masterbatch mix stage and the final mix stage. Various ingredients including the functionalized polymer of this invention can be added during these remills. Rubber compounding techniques and the additives employed therein are generally known as disclosed in Stephens, The Compounding and Vulcanization of Rubber, in Rubber Technology (2nd Ed. 1973).

The mixing conditions and procedures applicable to silica-filled tire formulations are also well known as described in U.S. Pat. Nos. 5,227,425, 5,719,207, 5,717,022, and European Patent No. 890,606, all of which are incorporated herein by reference. In one or more embodiments, where silica is employed as a filler (alone or in combination with other fillers), a coupling and/or shielding agent may be added to the rubber formulation during mixing. Useful coupling and shielding agents are disclosed in U.S. Pat. Nos. 3,842,111, 3,873,489, 3,978,103, 3,997,581, 4,002,594, 5,580,919, 5,583,245, 5,663,396, 5,674,932, 5,684,171, 5,684,172 5,696,197, 6,608,145, 6,667,362, 6,579,949, 6,590,017, 6,525,118, 6,342,552, and 6,683,135, which are incorporated herein by reference. In one embodiment, the initial masterbatch is prepared by including the functionalized polymer of this invention and silica in the substantial absence of coupling and shielding agents. It is believed that this procedure will enhance the opportunity that the functionalized polymer will react or interact with silica before competing with coupling or shielding agents, which can be added later curing remills.

Where the vulcanizable rubber compositions are employed in the manufacture of tires, these compositions can be processed into tire components according to ordinary tire manufacturing techniques including standard rubber shaping, molding and curing techniques. Typically, vulcanization is effected by heating the vulcanizable composition in a mold; e.g., it may be heated to about 140 to about 180° C. Cured or crosslinked rubber compositions may be referred to as vulcanizates, which generally contain three-dimensional polymeric networks that are thermoset. The other ingredients, such as processing aides and fillers, may be evenly dispersed throughout the vulcanized network. Pneumatic tires can be made as discussed in U.S. Pat. Nos. 5,866,171, 5,876,527, 5,931,211, and 5,971,046, which are incorporated herein by reference.

In order to demonstrate the practice of the present invention, the following examples have been prepared and tested. The examples should not, however, be viewed as limiting the scope of the invention. The claims will serve to define the invention.

EXAMPLES

Synthesis of Multifunctional Lithiated Amine-Containing Initiator and Novel Functional Polymers A dried 28-oz or 7-oz glass bottle, which previously had been sealed with extracted septum liners and perforated crown caps under a positive nitrogen purge, was used for all of the preparations. Butadiene in hexane (21.6 weight percent butadiene), styrene in hexane (33 weight percent styrene), hexane, n-butyllithium (1.60 M in hexane), 2-bis(2'-tetrahydrofuranyl)propane (OOPS) (1.60 M solution in hexane, stored over calcium hydride), and di-t-butyl-p-cresol solution in hexane (2 wt %) were used as supplied in the reactor room. Commercially available reagents and starting materials include the following: 4,4'-trimethylenedipiperidine (97%, Aldrich), N,N'-diethyl-1,3-propanediamine (97%, Aldrich), N,N'-diisopropyl-1,3-propanediamine (96%, Aldrich), N,N'-diethyl-2-butene-1,4-diamine (95%, Aldrich), tris[2-(methylamino)ethyl]amine (97%, Aldrich), and 1,5,9-triazacyclododecane (97%, Aldrich), N,N,N'-trimethylbis(hexamethylene)triamine (97%, Aldrich), N,N,N',N'-tetramethylethylenediamine (TMEDA, 99.5%, Aldrich), which were used as purchased without further purification.

Example 1

To a dried 28-oz glass bottle was added 83.3 g of hexane, and 166.7 g of 18.0 wt % butadiene in hexane, followed 0.34 ml of 4,4'-trimethylenedipiperidine solution (1.0 M in toluene) and 0.47 ml of n-BuLi (1.60M) in hexane by hypodermic syringe. The bottle was agitated and heated at 50° C. for 1.5 hr. After polymerization, the living cement was quenched by injection with 1.5 ml of isopropanol (i-PrOH), treated with an antioxidant (3 ml of 2 wt % di-t-butyl-p-cresol in hexane), coagulated in i-PrOH, then vacuum dried. Characterizations were performed, and the result was listed in Table 1, wherein Bd means butadiene; 1,2-Bd %, cis % of 1,4-Bd and trans of 1,4-Bd are analyzed by FT-IR; Mn means number average molecular weight; Mw means weight average molecular weight; Mp means peak molecular weight; PDI means polydispersity index (Mw/Mn); Tg means glass transition temperature. The molecule weight of the polymer in the example was determined by using a Waters Model 150-C GPC.

TABLE 1

| ID | Mn (g/mol) | Mw (g/mol) | Mp (g/mol) | PDI | Tg (° C.) | 1,2-Bd % | Cis % of 1,4-Bd | Trans % of 1,4-Bd |
|---|---|---|---|---|---|---|---|---|
| Example 1 | 84587 | 87468 | 88982 | 1.034 | −94.23 | 10 | 35.9 | 54.1 |

Example 2

The experimental in example 1 was repeated, however, with varied amount of randomizer of 2-bis(2'-tetrahydrofuranyl)propane (OOPS) and the effect of randomizer of 2-bis(2'-tetrahydrofuranyl)propane on polymer Tg (° C.) was listed in Table 2.

TABLE 2

| OOPS:"Li" (molar ratio) | Tg (° C.) |
|---|---|
| 0.00 | −94.23 |
| 0.15 | −46.52 |
| 0.25 | −39.24 |
| 0.35 | −33.89 |

Example 3

To a dried 28-oz glass bottle was added 91.7 g of hexane, and 208.3 g of 21.6 wt % butadiene in hexane, followed 0.61 ml of tris[2-(methylamino)ethyl]amine solution (1.0 M in toluene), 1.4 ml of N,N,N'N'-tetramethylethylenediamine (1.0M in hexane), and 1.15 ml of n-BuLi (1.60M) in hexane by hypodermic syringe. The bottle was agitated and heated at 50° C. for 1.5 hr. After polymerization, the living cement was quenched by injection with 1.5 ml of isopropanol (i-PrOH), treated with an antioxidant (3 ml of 2 wt % di-t-butyl-p-cresol in hexane), coagulated in i-PrOH, then vacuum dried. Characterizations were performed, and the result was listed in Table 3.

TABLE 3

| ID | Mn (g/mol) | Mw (g/mol) | Mp (g/mol) | PDI | Coupling (%) | Tg (° C.) |
|---|---|---|---|---|---|---|
| Example 3 | 69858 | 72166 | 73856 | 1.033 | 0 | −28.84 |

Example 4

To two gallons $N_2$ purged reactor equipped with a stirrer was added 1.565 kg of hexane, 0.412 kg of 33 wt % styrene in hexane and 2.508 kg of 21.7 wt % butadiene in hexane. The reactor was charged 3.0 ml of n-BuLi (1.60M) in hexane, and 1.0 ml of 1.6 M OOPS in hexane, and the reactor jacket was then heated to 50° C. After 30 minutes, the batch temperature peaked at 63.3° C. After an additional 30 minutes, the living cement was dropped into isopropanol containing butylated hydroxytoluene (BHT), and drum dried. The properties of the polymers are shown Table 4 and saved as control polymer.

TABLE 4

| ID | Mn (g/mol) | Mw (g/mol) | Mp (g/mol) | PDI | % Coupling | Tg (° C.) |
|---|---|---|---|---|---|---|
| SBR | 140235 | 145488 | 147178 | 1.037 | 0 | −37.76 |

Example 5

To two gallons $N_2$ purged reactor equipped with a stirrer was added 1.621 kg of hexane, 0.412 kg of 33 wt % styrene in hexane, and 2.452 kg of 22.2 wt % butadiene in hexane. The reactor was charged 3.09 ml of n-BuLi (1.60M) in hexane, and 1.0 ml of 1.6 M OOPS in hexane, the reactor jacket was then heated to 50° C. After 28 minutes, the batch temperature peaked at 61.2° C. After an additional 30 minutes, the living polymer was terminated with 5 ml of cyclohexanecarboxaldehyde homopiperidyhydrazone (CyAHPH, 1.0M in hexane) at 50° C. for 30 minutes, coagulated in isopropanol containing butylated hydroxytoluene (BHT), and drum dried. The properties of the polymers are shown in Table 5.

TABLE 5

| ID | Mn (g/mol) | Mw (g/mol) | Mp (g/mol) | PDI | % Coupling | Tg (° C.) |
|---|---|---|---|---|---|---|
| SBR-CyAHPH | 131403 | 135796 | 137507 | 1.033 | 0 | −37.87 |

Example 6

To two gallons $N_2$ purged reactor equipped with a stirrer was added 1.553 kg of hexane, 0.412 kg of 33 wt % styrene in hexane, and 2.519 kg of 21.6 wt % butadiene in hexane. The reactor was charged 6.30 ml of n-BuLi (1.60M) in hexane, 4.8 ml of 4,4'-trimethylenedipiperidine solution (TMDP, 1.0 M in toluene) and 2.8 ml of N,N,N',N'-tetramethylethylenediamine (TMEDA, 1.0M in hexane), the reactor jacket was then heated to 50° C. After 26 minutes, the batch temperature peaked at 63.3° C. After an additional 30 minutes, the living polymer was terminated with 10.1 ml of cyclohexanecarboxaldehyde homopiperidyhydrazone (CyAHPH, 1.0M in hexane) at 50° C. for 30 minutes, coagulated in isopropanol containing butylated hydroxytoluene (BHT), and drum dried. The properties of the polymers are shown in Table 6.

TABLE 6

| ID | Mn (g/mol) | Mw (g/mol) | Mp (g/mol) | PDI | % Coupling | Tg (° C.) |
|---|---|---|---|---|---|---|
| CyAHPH-TMDP-CyAHPH | 135610 | 152823 | 138573 | 1.127 | 10.62 | −34.29 |

Application in Rubber Compounds

Rubber compounds having the formulation shown in Table 7 was prepared to demonstrate the beneficial properties of the rubber compounds contains a polymer synthesized by the multifunction lithiated amine-containing initiators of the embodiments of the invention.

TABLE 7

| Compound formulation, carbon black only All CB with Black Oil | |
|---|---|
| Masterbatch | Amount (phr) |
| Polymer | 100 |
| CB (N343) | 50 |
| Wax | 2 |
| Black oil | 10 |
| Stearic acid | 2 |
| N-phenyl-N'-(1,3-dimethylbutyl)-p-phenylenediamine (6PPD) | 0.95 |
| N-stage sub | 164.95 |
| Final | 164.95 |
| N-stage | |
| Sulfur | 1.5 |
| N-t-butylbenzothiazole-2-sulfenamide (TBBS) | 0.5 |

TABLE 7-continued

Compound formulation, carbon black only
All CB with Black Oil

| Masterbatch | Amount (phr) |
|---|---|
| 2,2'-dithiobisbenzothiazole (MBTS) | 0.5 |
| N,N'-diphenylguanidine (DPG) | 0.3 |
| ZnO | 2.5 |
| Final total | 170.25 |

The polymer synthesized above Example 4~6 was employed to prepare vulcanizable rubber compositions, cured, and analyzed for various physical and dynamic properties. Results of physical testing on these compounds are shown below in Table 8.

From the data of Table 8, one can see that styrene/butadiene interpolymers having terminal —NH—NR$^1$R$^2$ functional group on both polymer ends can provide excellent combinations of physical properties such as 50° C. strain sweep tan δ (an indicator of reduced hysteresis), bound rubber, modulus, tensile strength, ΔG', etc., in carbon black-only formulations Compared to a control interpolymer (Example 4) and one-end functional polymer (Example 5), such functionalized interpolymers can exhibit significant reductions in tan δ, up to ~70% (compare Example 6 to Example 4).

TABLE 8

Testing data from Examples 4-6

|  | 4 | 5 | 6 |
|---|---|---|---|
| M$_n$ (kg/mol) | 140 | 131 | 136 |
| M$_w$/M$_n$ | 1.04 | 1.03 | 1.13 |
| % coupling | 0 | 0.0 | 10.6 |
| T$_g$ (° C.) | −37.8 | −37.9 | −33.0 |
| Dispersion index | 96.6 | 96.1 | 95.1 |
| Bound rubber (%) | 11.3 | 30.1 | 37.1 |
| 171° C. MDR t$_{50}$ (min) | 2.52 | 2.00 | 1.62 |
| 171° C. MH-ML (kg-cm) | 16.84 | 14.65 | 13.03 |
| ML$_{1+4}$ @ 100° C. | 54.5 | 83.7 | 108.5 |
| 200% modulus @ 23° C. (MPa) | 7.88 | 8.73 | 8.25 |
| Tensile strength @ 23° C. (MPa) | 19.8 | 20.2 | 11.7 |
| Temp. sweep 0° C. tan δ | 0.374 | 0.403 | 0.382 |
| Temp. sweep 60° C. tan δ | 0.197 | 0.137 | 0.073 |
| RDA 0.25-14% ΔG' (MPa) | 3.399 | 0.354 | 0.387 |
| 60° C. RDA strain sweep (5% strain) tan δ | 0.2122 | 0.1039 | 0.0631 |
| 60° C. Dynastat tan δ | 0.1913 | 0.0996 | 0.0633 |

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A method of preparing a polymer by employing anionic polymerization comprising the steps of:
   (i) providing at least one conjugated diene monomer;
   (ii) providing an initiator comprising a multifunctional lithiated amine-containing compound comprising at least two lithiated amine groups per molecule of the compound, wherein the multifunctional lithiated amine-containing compound is Li-4,4'-trimethylenedipiperidine-Li; and
   (iii) contacting the monomer and the initiator.

2. The method of claim 1, wherein contacting the monomer and initiator results in a living polymer, and further comprising the step of contacting the living polymer with a polymerization terminator.

3. The method of claim 1, further comprising the step of providing at least one vinyl aromatic monomer.

4. The method of claim 1, further comprising the step of isolating the polymer formed in step (iii).

5. A method of preparing a polymer by employing anionic polymerization comprising the steps of:
   (i) providing at least one conjugated diene monomer;
   (ii) providing an initiator comprising a multifunctional lithiated amine-containing compound comprising at least two lithiated amine groups per molecule of the compound, the multifunctional lithiated amine-containing compound having the following formula:

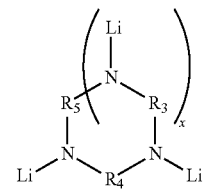

wherein x is 1 or more and wherein R$_3$, R$_4$, and R$_5$ are the same or different and represent alkylene groups containing from 3 to 20 carbon atoms; and
   (iii) contacting the monomer and the initiator.

6. The method of claim 5, wherein the initiator is generated in-situ during the preparation of the polymer.

7. The method of claim 5, wherein contacting the monomer and the initiator results in a living polymer, and further comprising the step of contacting the living polymer with a polymerization terminator.

8. The method of claim 5, further comprising the step of providing at least one vinyl aromatic monomer.

9. The method of claim 5, further comprising the step of isolating the polymer formed in step (iii).

10. A method of preparing a polymer by employing anionic polymerization comprising the steps of:
    (i) providing at least one conjugated diene monomer;
    (ii) generating an initiator in-situ where the initiator comprises a multifunctional lithiated amine-containing compound comprising at least two lithiated amine groups per molecule of the compound, wherein the multifunctional lithiated amine-containing compound is Li-4,4'-trimethylenedipiperidine-Li; and
    (iii) contacting the monomer and the initiator.

11. The method of claim 10, wherein the initiator is soluble in hexane without the addition of any polar additive.

12. The method of claim 10, wherein contacting the monomer and the initiator results in a living polymer, and further comprising the step of contacting the living polymer with a polymerization terminator.

13. The method of claim 10, further comprising the step of providing at least one vinyl aromatic monomer.

14. The method of claim 10, further comprising the step of isolating the polymer formed in step (iii).

* * * * *

UNITED STATES PATENT AND TRADEMARK OFFICE
CERTIFICATE OF CORRECTION

| | |
|---|---|
| PATENT NO. | : 8,362,164 B2 |
| APPLICATION NO. | : 13/271922 |
| DATED | : January 29, 2013 |
| INVENTOR(S) | : Yan |

It is certified that error appears in the above-identified patent and that said Letters Patent is hereby corrected as shown below:

On the Title page of the patent, Item (75) the First Inventor should read -- Yuan-Yong Yan --.

Signed and Sealed this
Thirtieth Day of July, 2013

Teresa Stanek Rea
*Acting Director of the United States Patent and Trademark Office*